(12) United States Patent
Chornet et al.

(10) Patent No.: US 6,964,772 B1
(45) Date of Patent: Nov. 15, 2005

(54) CHITOSAN-XANTHAN BASED POLYIONIC HYDROGELS FOR STABILIZATION AND CONTROLLED RELEASE OF VITAMINS

(75) Inventors: Esteban Chornet, Sherbrooke (CA); Severian Dumitriu, Sherbrooke (CA)

(73) Assignee: Kemestrie Inc., Sherbrooke (CA)

( * ) Notice: Subject to any disclaimer, the term of this patent is extended or adjusted under 35 U.S.C. 154(b) by 0 days.

(21) Appl. No.: 09/301,670

(22) Filed: Apr. 28, 1999

(30) Foreign Application Priority Data

Jul. 17, 1998 (CA) .............................. 2243619

(51) Int. Cl.$^7$ .......................... A61K 9/107; A61K 47/36
(52) U.S. Cl. ....................... 424/400; 514/938; 514/777; 514/782
(58) Field of Search ............................... 424/484, 486, 424/488, 499–501; 514/944, 937–38, 844, 846, 777, 782

(56) References Cited

U.S. PATENT DOCUMENTS

| 4,778,749 A | * 10/1988 | Vasington et al. |
| 5,620,706 A | 4/1997 | Dumitriu et al. |

FOREIGN PATENT DOCUMENTS

| EP | 279319 | 8/1988 |
| EP | 0 504 066 B1 | 9/1996 |

OTHER PUBLICATIONS

S. Dumitriu, E. Chornet, "Functional versatility of polyionic hydrogesl", Chitin Enzymology, Vo 2, 1996, R.A.A. Muzzarelli, ed. Atec Edizioni, Italy, p. 543–564.

S. Dimitriu, E. Chornet, "Polysaccharides as support for enzymes and cell immobilization", in POLYSACCHARIDES, S. Dumitriu, Ed. Marcel Dekker, Inc., New York, 1998, p. 629–749.

N. Kubota, Y. Kikuchi, "Macromolecular complexes of chitosan", in POLYSACCHARIDES, S. Dumitriu, Ed. Marcel Dekker, Inc., New York, 1998, p. 595–629.

S. Dumitriu, P. Magny, D. Montane, P.F. Vidal, E. Chornet, "Polyionic hydrogels obtained by complexation between xanthan and chitosan: their properties as supports for enzyme immobilization", J. Bioactive and Compatible Polymers, 9, 184–209 (1994).

S. Dumitriu, P.F. Vidal, E. Chornet, "Hydrogels based on polysaccharides", in Polysaccharides in Medicinal Applications, S. Dumitriu, Ed Marcel Dekker, Inc., New York, 1996, p. 125–241.

S. Dumitriu, M. Dumitriu, "Hydrogels as support for drug delivery systems", in Polysaccharides in Medicinal Applications, S. Dumitriu, Ed. Marcel Dekker, Inc., New York, 1996, p. 705–764.

S. Dumitriu, E. Chornet, "Polyionic Hydrogels as supports for enzyme immobilization", in Chitin Enzymology vol. 2, R.A.A. Muzzarelli, Ed. Atec Endizioni, Italy, 1996, p. 527–542.

S. Dumitriu, E. Chornet, "Immobilization of xylanase in chitosan–xanthan hydrogels", Biotechnol. Prog., 13, p. 539–545 (1997).

* cited by examiner

*Primary Examiner*—Edward J. Webman
(74) *Attorney, Agent, or Firm*—Goudreau Gage Dubuc

(57) ABSTRACT

A thermo- and photo stable composition comprising a chitosan/xanthan hydrogel including at least one thermo- or photo-sensitive substance chosen among the following: vitamins, amino-acids, nucleic acids, and polypeptides. The hydrogel can be adapted to release the thermo- or photo-sensible substances in either a human or an animal. The present invention also discloses a method of making these hydrogel composition. Additionally, the present invention presents a method of using these hydrogel composition in dermatology or as a food supplement.

9 Claims, 7 Drawing Sheets

CHITOSAN-XANTHAN BASED POLYIONIC HYDROGELS FOR STABILIZATION AND CONTROLLED RELEASE OF VITAMINS

FIELD OF THE INVENTION

The present invention relates to chitosan/xanthan based hydrogels. More specifically, the present invention deals with chitosan/xanthan based hydrogels used in dermatology and as food additives, where such hydrogels are used as carrier for active compounds such as vitamins, amino-acids, nucleic acids, polypeptides, etc.

BACKGROUND OF THE INVENTION

The production of chitosan/xanthan hydrogels is known. U.S. Pat. Nos. 5,620,706 and 5,648,252 describe such hydrogels as inert supports for enzyme immobilisation or for the controlled release of specific antibiotics or anticancer agents. However, the application of such hydrogels as supports, stabilisation and subsequent controlled release of vitamins, amino-acids, nucleic acids and polypeptides has not been proposed yet.

One of the key aspects in the preparation of food additives and dermatological preparations is the preservation of active ingredients prone to degradation, such as vitamins, amino-acids, nucleic acids and polypeptides. Exposure of such ingredients to heat or light accelerates their degradation.

Given the importance of the active ingredients mentioned above, several excipients, such as tablets, capsules, gellules, gels, lotions, ointments, emulsions and simple solutions, have been developed with a view to protect the active ingredients against degradation or simply to render them hydrophobic. However, several drawbacks of these synthetic devices have been identified. In particular their irritation potential and toxicity were put forward.

Due to the inherent limitations of conventional excipients, the use of synthetic polycations was recently proposed. As an example, European patent application # 504 066 A1, 1992, to L'Oréal (France) proposes cosmetic compositions comprising a dispersion of active solid particles coated with a cationic polymer. The aim of the polymeric coating being to increase the stability of the overall composition in addition to preventing degradation of the active ingredient.

Yet an important objective remains unfulfilled. Indeed, there remains an important need to develop new excipients capable of being used in food and dermatological preparations to stabilise thermo- or photo sensitive active ingredients, such as vitamins, nucleic acids, amino-acids and polypeptides.

OBJECTS OF THE INVENTION

An object of the present invention is therefore to provide a hydrogel preparation for use as a delivery device for food or dermatological preparations with a concurrent objects of providing stabilization of thermo- and photo sensitive active ingredients and avoiding any irritation or toxicity potentials. A further object of the present invention is to disclose a method of dispersion of the active ingredient within the hydrogel matrix.

SUMMARY OF THE INVENTION

Generally, in accordance with the present invention, there is provided a preparation which stabilises thermo- and photo sensitive bioactive molecules. The preparation comprises a hydrogel made of a complex of chitosan and xanthan. Within the hydrogel there is lodged at least one thermo- or photo sensitive substance chosen among the following: vitamins, amino-acids, nucleic acids and polypeptides. The hydrogel configuration and structure is prepared so as to release, in a controlled way, the thermo- or photo sensitive ingredients either in a human or animal subjects.

The present invention also discloses a method of making these hydrogels. The present invention also teaches the use of these hydrogels in dermatology or as a food additive vehicle.

Other objects, advantages and features of the present invention will become more apparent upon reading of the following non restrictive description of preferred embodiments thereof, given by way of example only with reference to the accompanying drawings.

Those specialised in the area covered by this invention will certainly be able to apply modifications or adaptations to the details described in the preferred embodiment while being constrained within the framework of the current invention.

DESCRIPTION OF THE PREFERRED EMBODIMENT

The detailed description reveals compositions for food and dermatological applications comprising one or several active ingredients that are either prone to thermo- or photo degradation. These compositions are based on a polyionic hydrogels obtained by a chitosan/ xanthan complexing which incorporates therein the active ingredients thereby protecting them from thermo- or photo induced degradation while controlling their release thus enhancing their activity and the duration of this activity.

Also described are two methods of incorporation of the active ingredients in the hydrogel depending on the nature of the active ingredients. In a first method, liposoluble active ingredients are introduced in the hydrogel during the making of the hydrogel. In a second method, hydrosoluble active ingredients are introduced by diffusion in the already made hydrogel. Both methods can be used in sequence.

The present invention thus reveals a novel and surprising way of introducing various vitamins and other ingredients such as amino-acids, nucleic acids and polypeptides in hydrogels and of controlling the release of those ingredients in various drug delivery vehicles such as: capsules or gelcaps for oral ingestion, rectal suppositories, creams and ointments, gels, solutions and cutaneous patches.

The present invention further reveals a method of introducing in the same hydrogel liposoluble and hydrosoluble active ingredients.

Finally, the present invention further discloses methods of making food additives and dermatological creams incorporating the hydrogel.

It is to be noted that the terms "dermatologic" and "dermatological" are used in their widest sense thus covering both the dermatological and cosmetic applications. Furthermore, these terms are meant to cover direct skin treatments or treatment through nails or hair.

The term "food additive" is also to be understood in its widest sense including thus all food preparations where the additive has a nutritional or therapeutic function as well as simple mechanical functions such as that of a texturizing agent, filler or viscosity control agent.

The preparations covered by the present invention focus mainly on humans although they may be used in the veterinary field.

Figure 1:
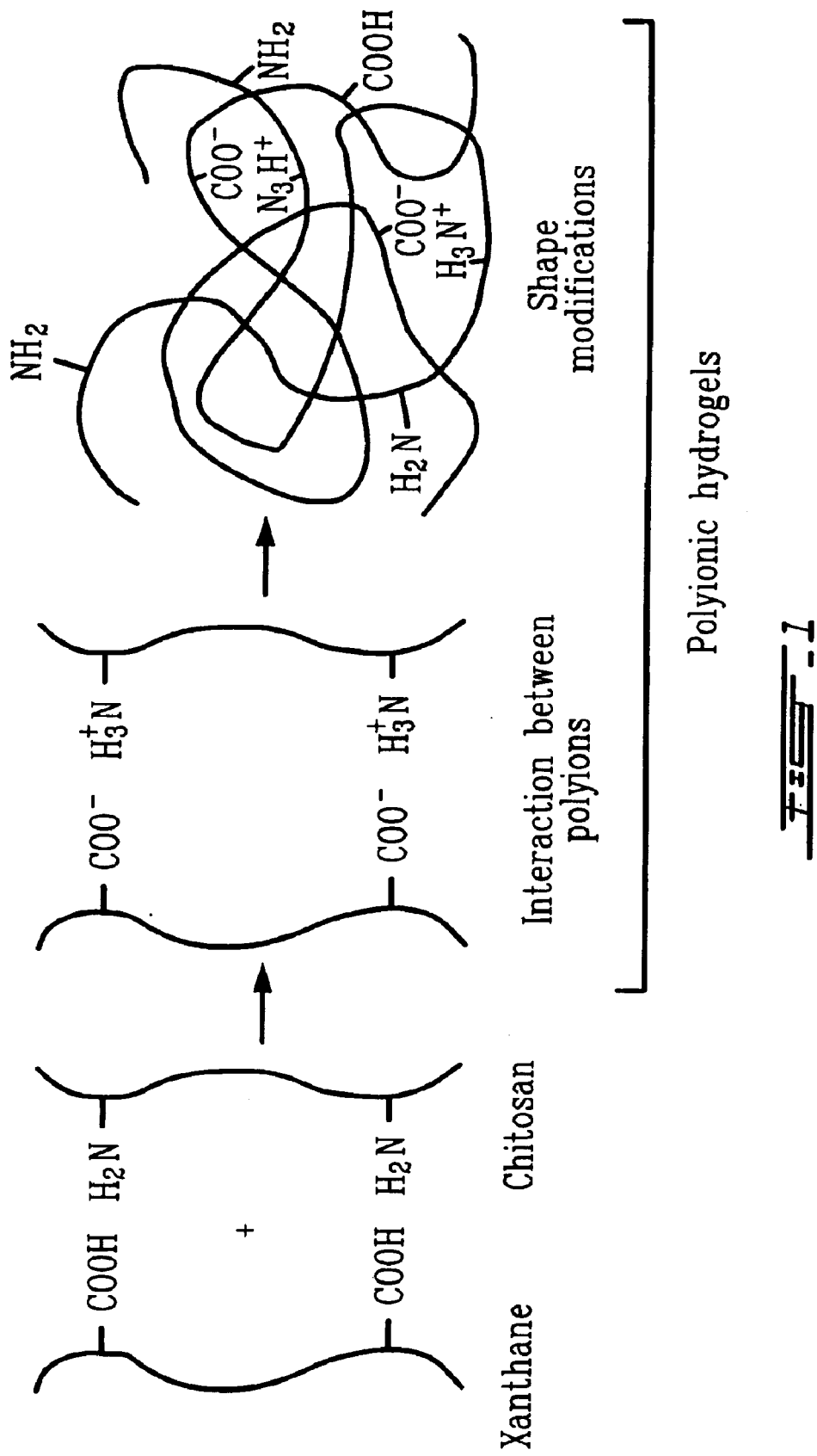
FIG. 1 is a complex of chitosan and xanthan.

On FIG. 1, it is shown how the hydrogel of the present invention is an ionic complex between chitosan, a cationic natural polymer, and xanthan, an anionic natural polymer. A method of making of the hydrogel has been described in U.S. Pat. No. 5,720,206 granted to the same assignee as in the present application and is incorporated herein by reference. As shown in FIG. 1, xanthan and chitosan form a complex, i.e. a network of ionic linkages between these two polymer molecules. The complex is a highly hydrophilic hydrogel.

(a) Inclusion of liposoluble vitamins in the chitosan-xanthan hydrogel

Vitamin A, also called Retinol, is a molecule extremely sensitive to light and oxygen. As a consequence, this vitamin may not be used in a cream unless it is being stabilised to counteract the negative effects of light and oxygen (from ambient air). The method of the present invention consists in stabilising Vitamin A in a hydrogel made of xanthan and chitosan complex. The xanthan and chitosan complex being described in U.S. Pat. No. 5,620,706.

EXAMPLE 1

Inclusion of Vitamin A when making the hydrogel

A solution (100 ml) of Vitamin A (10–20 w/v %) in ethanol is first prepared. This solution is added, under intense agitation, to 500 ml of a xanthan solution, 0.65 w/v %. The final solution has a Vitamin A concentration between 1.66 and 3.33 w/v %. The solution is kept at 3° C. It is subsequently sprayed, via a nozzle, into 800 ml of a 0.65 w/v % chitosan solution. The complexation reaction is conducted during 30 minutes. The gel formed is then filtered and rinsed with water to a pH of 6.8. In order to increase the hydrogel stability, a final washing with a sodium bicarbonate solution, 1 w/v %, brings the gel to a pH of 7.5. The gel is then frozen and freeze-dried. All these operations, including the freeze drying, are best conducted in the absence of light and oxygen.

EXAMPLE 2

Inclusion of Vitamin A by diffusion

Using a previously prepared xanthan-chitosan hydrogel with a swelling index ($\alpha$) of at least 2000%, it is possible to introduce the Vitamin A by diffusion. The swelling index ($\alpha$) is defined as follows:

$$\alpha = 100\% \times \text{mass of swelled hydrogel in equilibrium} - \text{mass of dried hydrogel mass of dried hydrogel}$$

Under these conditions, the time for the experiment is decreased thereby preventing the molecule's degradation. The method involves dissolving 0.07 g of Vitamin A in 1 ml of ethanol (96%) and adding 1.5 g of the freeze dried xanthan-chitosan complex having $\alpha=2500\%$. Slight agitation allows the obtention of a homogeneous paste. 2 ml of ethanol, and 200 µl of water are then added under slight agitation and the mixture is kept at 4° C. for 24 hours in absence of light. The alcohol is then evaporated, at 4° C. The final product can be freeze dried and has 46 mg of Vitamin A per g of freeze dried xanthan-chitosan complex.

EXAMPLE 3

Inclusion of Vitamin E

The method (a) developed for Vitamin A is also applied for the inclusion of Vitamin E. The concentration of Vitamin E in the freeze dried hydrogel can reach 20 wt %.

EXAMPLE 4

Inclusion of Vitamin K

The method (a) developed for Vitamin A is also applied for the inclusion of Vitamin K. The concentration of Vitamin K in the freeze dried hydrogel can reach 20 wt %.

(b) Inclusion of hydrosoluble vitamins in the chitosan-xanthan hydrogel

For bioactive hydrosoluble ingredients, it is preferable to use the diffusion method in the freeze dried hydrogel to avoid loss of ingredients that would otherwise occur during the reaction between xanthan and chitosan. In this method, the xanthan-chitosan hydrogel must have a swelling index of at least 2000%.

EXAMPLE 5

Inclusion of Vitamin C

Given the redox character of Vitamin C with regards to chitosan, a new method of inclusion has been developed. This method involves 2 steps:

Step 1: Preparation of the xanthan-chitosan complex (CHITOXAN™), i.e. the polyonic hydrogel;

Step 2: Incorporation of Vitamin C.

Step 1- Preparation of the xanthan-chitosan complex

Step 1 follows the method described in U.S. Pat. No. 5,620,706. Chitosan used has typically a molecular weight comprised between 250,000 and 350,000 and the hydrogel produced a swelling index of $\alpha>2000\%$. The CHITOXAN™ thus produced is milled to obtain a fine powder of particles comprised between 250 and 500 µm.

Step 2 - Incorporation of Vitamin C

This step can be carried out via two different approaches:

2a. Stabilisation with amino-acids

To 10 ml of water are added 1 g of Vitamin C, 0.06 g of L-cysteine, 0.02 g of L-cystine and 0.02 g of L-methionine. To this solution, 1 g of freeze-dried CHITOXAN™ made of particles having diameters comprised between 250 and 500 µm is added. It is not necessary that the mixture have any excess liquid. Pure water may be added to complete the hydration for a period of 2 hours. All the operations preferably require the absence of light. The mixture is then frozen, freeze-dried and milled to provide a final product made of particles having diameters comprised between 50 and 125 µm.

The Vitamin C thus incorporated in the freeze-dried hydrogel and hydrated shows a good stability, without coloration after 2 weeks at 45° C. (wet hydrogel) and after 20 weeks at 45° C. (dried hydrogel). It is also possible to use as "stabilisers" either tartaric acid at 0.1 wt %, metaphosphoric acid at 0.03 wt % or citric acid at 0.1 wt %. The percentage is expressed with respect to CHITOXAN™.

2b. Stabilisation with tripeptides

The previous method (2a) is used replacing the three amino-acids with a tripeptide having sulfur-containing functionalities. To 10 ml of water, g of Vitamin C and 0.002 g of glutathione are added. After 5 minutes of agitation, 1 g of CHITOXAN™ is added. The mixture is kept in slight agitation until a homogeneous paste is obtained. The mixture is left to stand for 2 hours to reach the equilibrium hydration. The paste is then frozen and freeze-dried. All operations preferably require absence of light.

(c) Extraction and determination of Vitamin C included in CHITOXAN™

Extraction

The solvent used is an aqueous mixture of 3% (w/v) metaphosphoric acid and 8% (v/v) acetic acid.

The method consists of introducing 20 to 30 mg of freeze-dried CHITOXAN™ loaded with Vitamin C in a 50 ml centrifuge tube together with 40 ml of the extraction solvent. The mixture is magnetically stirred for 60 minutes. The suspension formed is centrifuged (4000 rpm) and the supernatant is analysed. All operations are done in absence of light.

Analytical determination of Vitamin C

This determination requires the establishment of a calibration curve at a maximum absorption wavelength using a UV-vis spectrophotometer. A standard is prepared with the same solution (and solvent) initially used to introduce the Vitamin C within the CHITOXAN™. Experimentation has shown an absorption maximum at 243 nm for Vitamin C at 98% purity obtained from ALDRICH.

The calibration curve is constructed at 243 nm as follows. A solution of 1.3 mg/ml of Vitamin C in the solvent is prepared in a graduated cylinder. The solution is prepared just before analysis. By successive dilutions, the absorption versus concentration calibration curve (mg/ml) is thus measured.

The concentration of Vitamin C in the supernatant obtained via extraction is determined at 243 nm using the calibration curve. The concentration of Vitamin C in the sample prepared by method 2a is 49.6%.

(d) Inclusion of the CHITOSAN™ —Vit. C preparation in a cream 1 g of CHITOXAN™ —Vit. C preparation is hydrated with water until a creamy paste is obtained. Weighing the paste permits to calculate the amount of Vitamin C present. Subsequently, the paste is mixed, under strong agitation, with a base cream in order to achieve a final concentration in Vitamin C preferably comprised between 5 and 25 wt %.

(e) Determination of the Vitamin C stability in the cream base 10 g of the preparation obtained by inclusion of CHITOXAN™—Vit. C in a cream base is introduced in a glass tube protected from exposure to light. The tube is heated at 45° C. In order to determine the rate of degradation of Vitamin C in the base cream, an aliquot is taken corresponding to a total amount of 10 to 30 mg of Vitamin C. Such an aliquot is taken every day for the first four (4) days and, subsequently, every other day for a total of 30 days. Samples not immediately analysed were kept frozen at −4° C.

The aliquots were analysed with the method described earlier (always using the extraction solvent).

With samples VS2L, VS2R and VS2M, were prepared creams having concentrations of Vitamin C comprised between 5 and 25 wt %. Using the method previously described, Vitamin C inserted in CHITOXAN™ was found to be stable with no coloration of the cream appearing after 30 days at 45° C. and the degradation of the Vitamin C was as little as 15 %. With a cream prepared with free Vitamin C (i.e. no hydrogel), an orange coloration appeared and a 98% degradation of Vitamin C occurred under the same conditions.

(f) Controlled release kinetics

Figure 2:
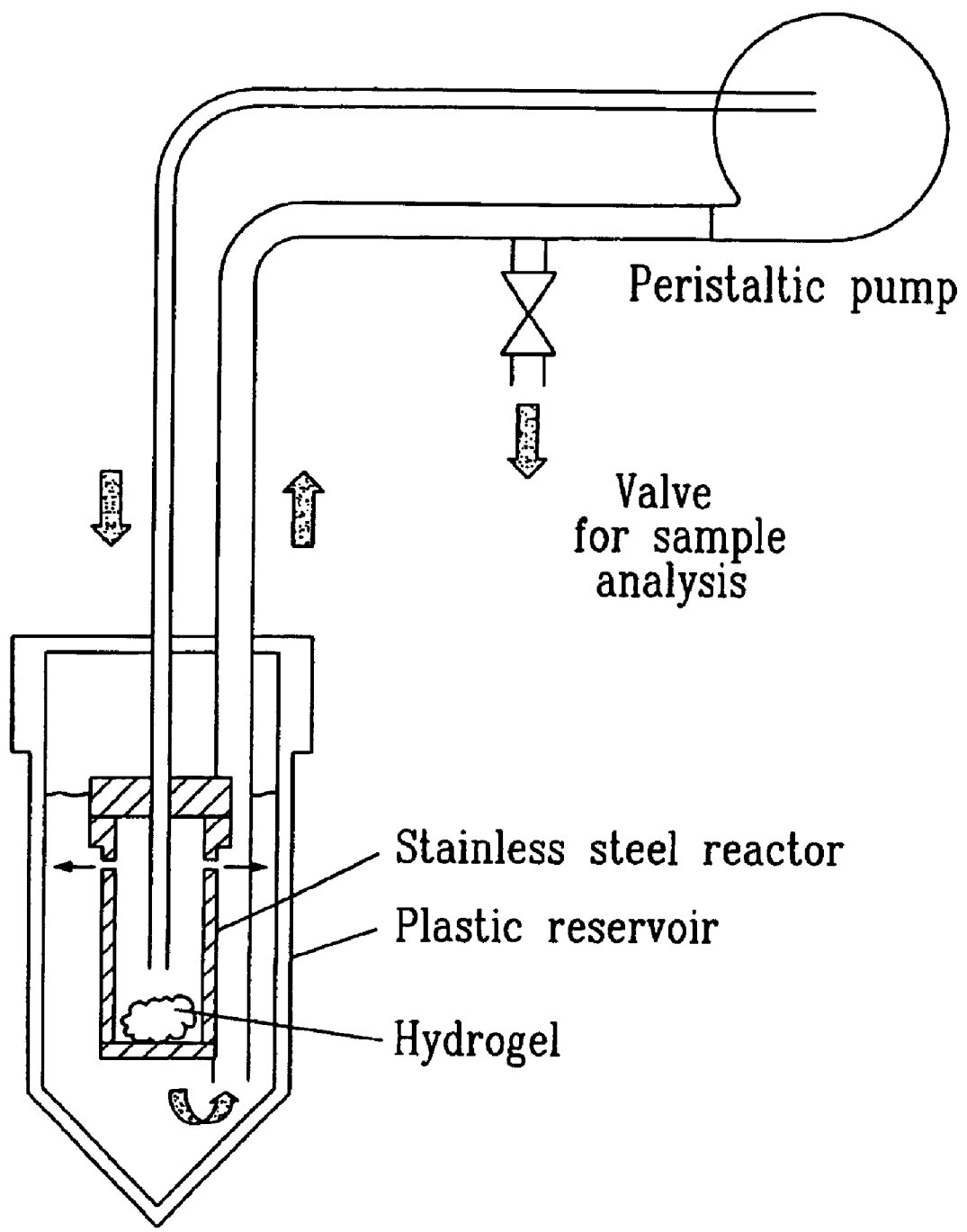
FIG. 2 is a diagram of the lab apparatus for kinetic studies.

Table 1 shows the types of CHITOXAN™ —Vit. C combinations studied. As illustrated in FIG. 2, the controlled release kinetics is determined by introducing a precise quantity of the CHITOSAN™ —Vit. C preparation in the reactor.

TABLE 1

Types of CHITOXAN ™ - Vit. C preparations studied

| Preparations Codes CHITOXAN ™ - Vit. C | Swelling index (α) of CHITOXAN ™ % | Concentration of Vit. C in the CHITOXAN ™ - Vit. C (wt %) |
|---|---|---|
| VS2L | 1800 | 50.3 |
| VS2R | 2200 | 49.6 |
| VS2M | 3500 | 51.0 |

The solvent, a mixture of 3% w/v methaphosphoric acid and 8% w/v acetic acid, flows into the central tube directly into the reactor where it comes into contact with the CHITOXAN™ —Vit. C preparation. The Vitamin C is gradually released from the preparation and solubilizes inside the solvent. The latter leaves the reactor through small orifices ensuring constant circulation of the solvent and good contact with the preparation.

Figure 3:
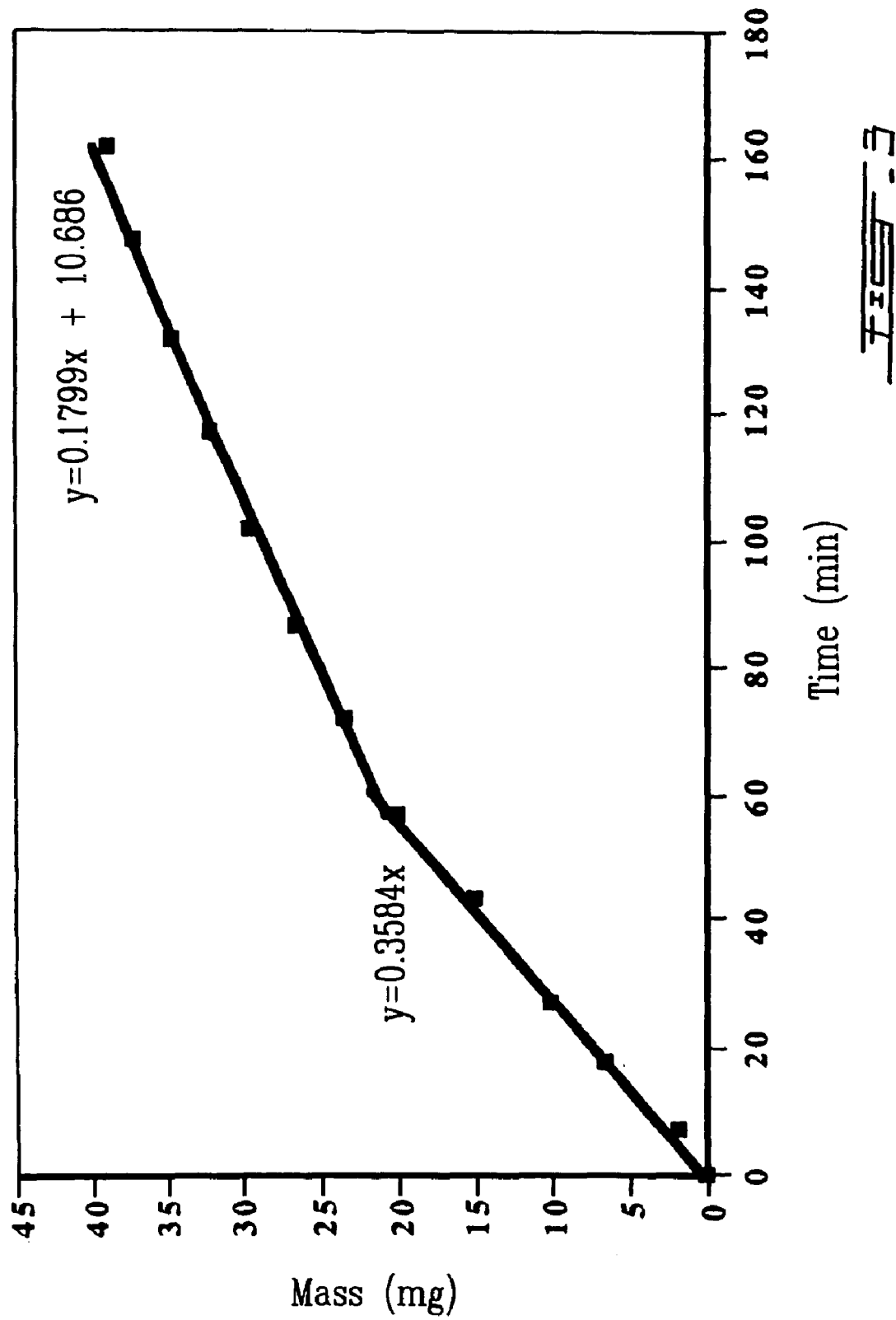
FIG. 3 is an amount of Vitamin C released as a function of time/ Sample coded VS2L. The hydrogel CHITOXAN™ —Vitamin C is prepared with CHITOXAN™ having a swelling index ($\alpha$) of 1800%.
Figure 4:
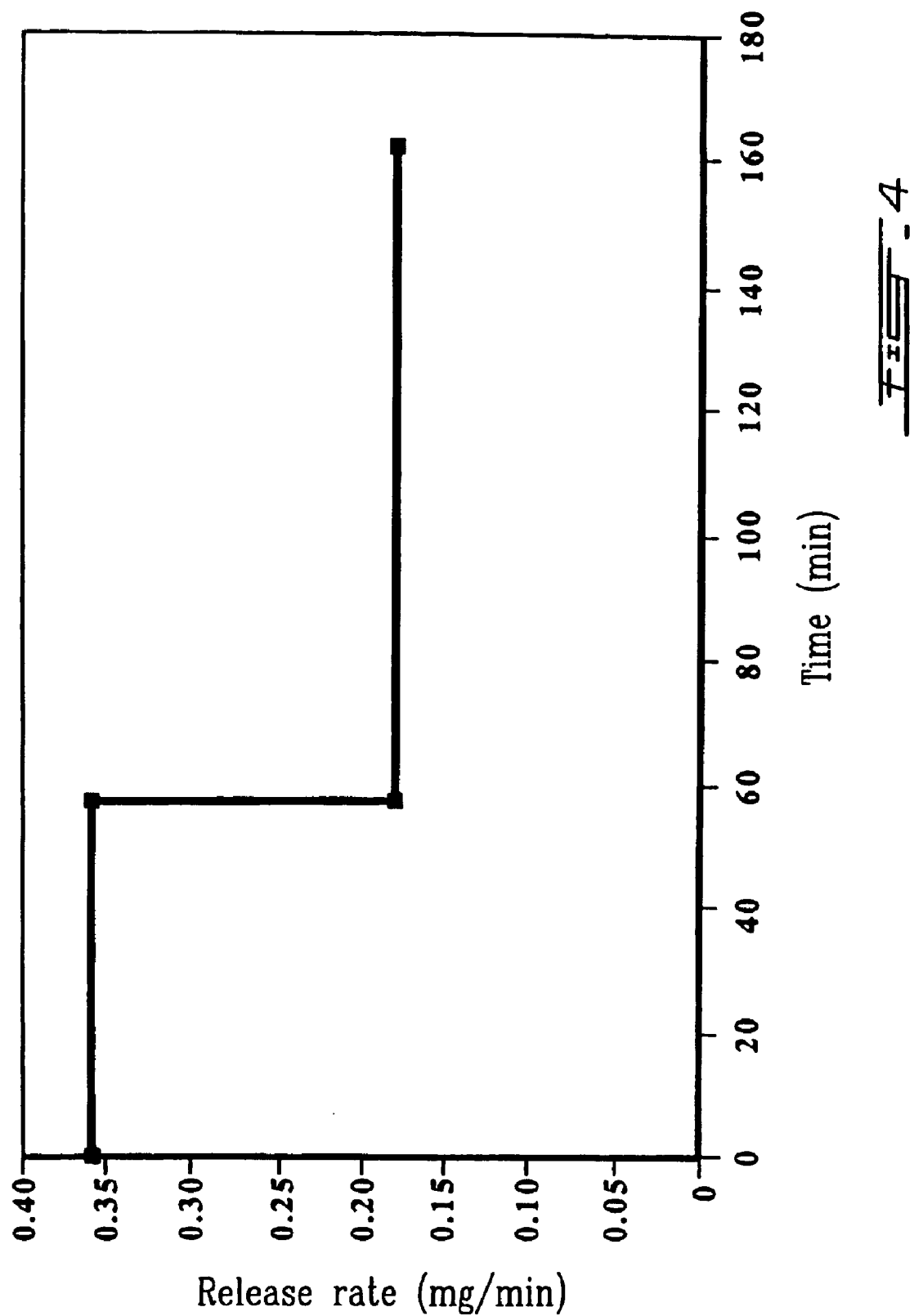
FIG. 4 is the rate of release of Vitamin C as a function of time. Sample coded VS2L.

FIG. 3 shows that the Vitamin C released from sample VS2L follows a linear increase as a function of time with two distinct slopes, depicted in FIG. 4.

FIG. 4 shows that with sample VS2L, the Vitamin C diffuses at a constant speed of 0.36 mg/min during the first period while it decreases by half for the 100 following minutes.

Figure 5:
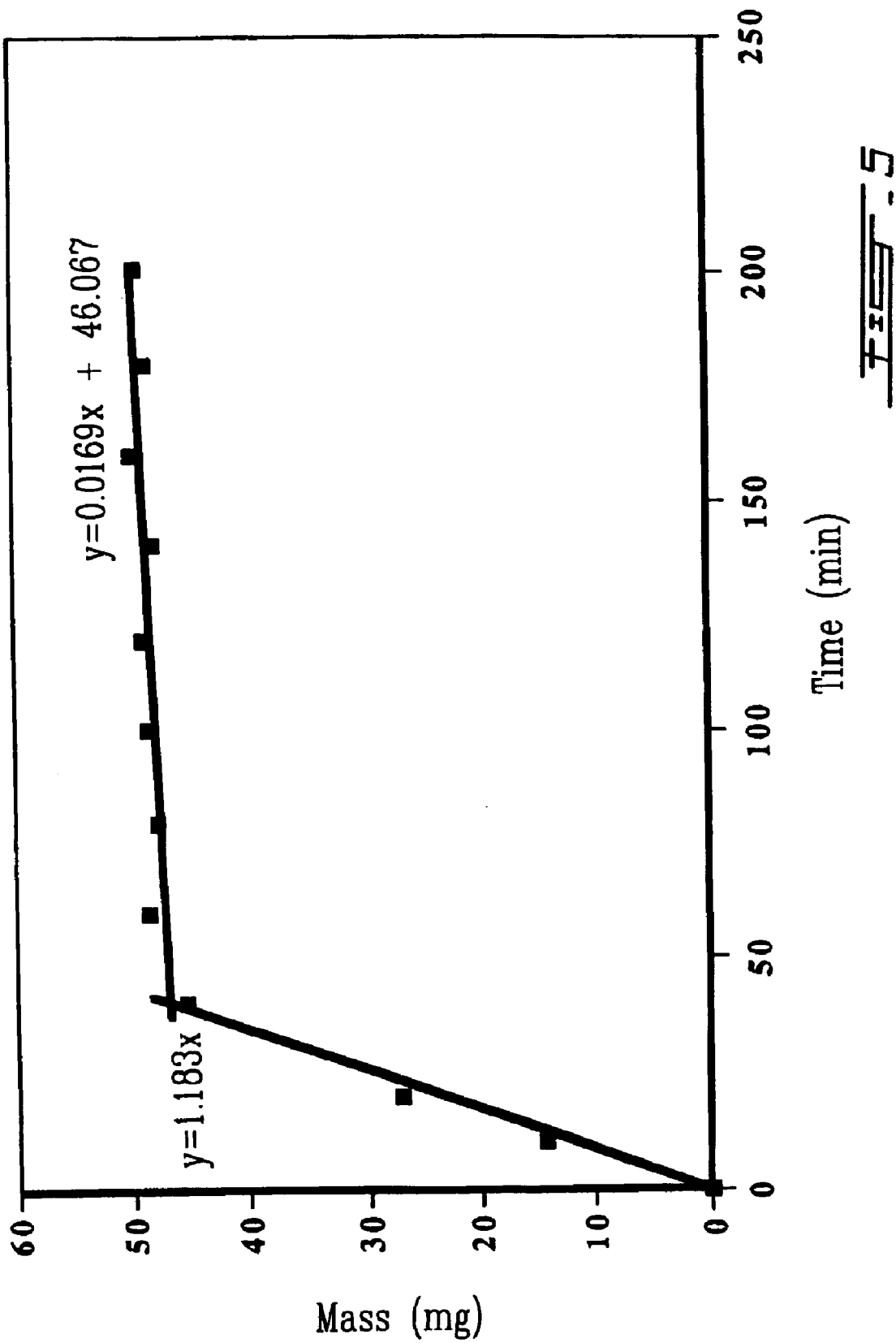
FIG. 5 is the amount of Vitamin C released as a function of time/ Sample coded VS2R. The hydrogel CHITOXAN™ —Vitamin C is prepared with CHITOXAN™ having a swelling index ($\alpha$) of 2200%.
Figure 6:
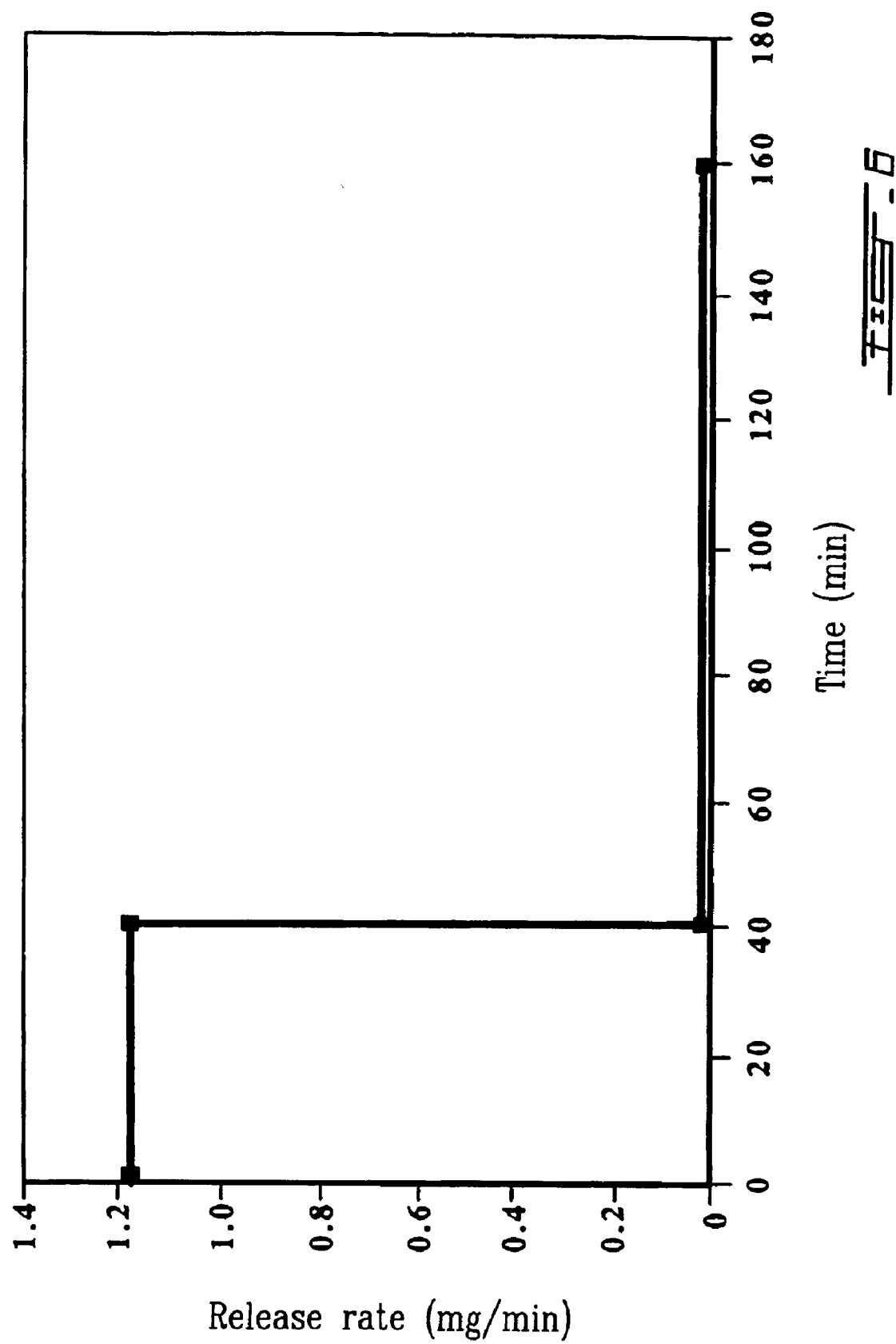
FIG. 6 is the rate of release of Vitamin C as a function of time. Sample coded VS2R.

Sample VS2R also shows in FIG. 5 the two distinct linear increase profiles with two distinct slopes depicted in FIG. 6. The first slope is faster than that of preparation VS2L indicating a more rapid liberation. The second slope, at 0.02 mg/min, releases Vitamin C at a controlled but slow rate.

Figure 7:
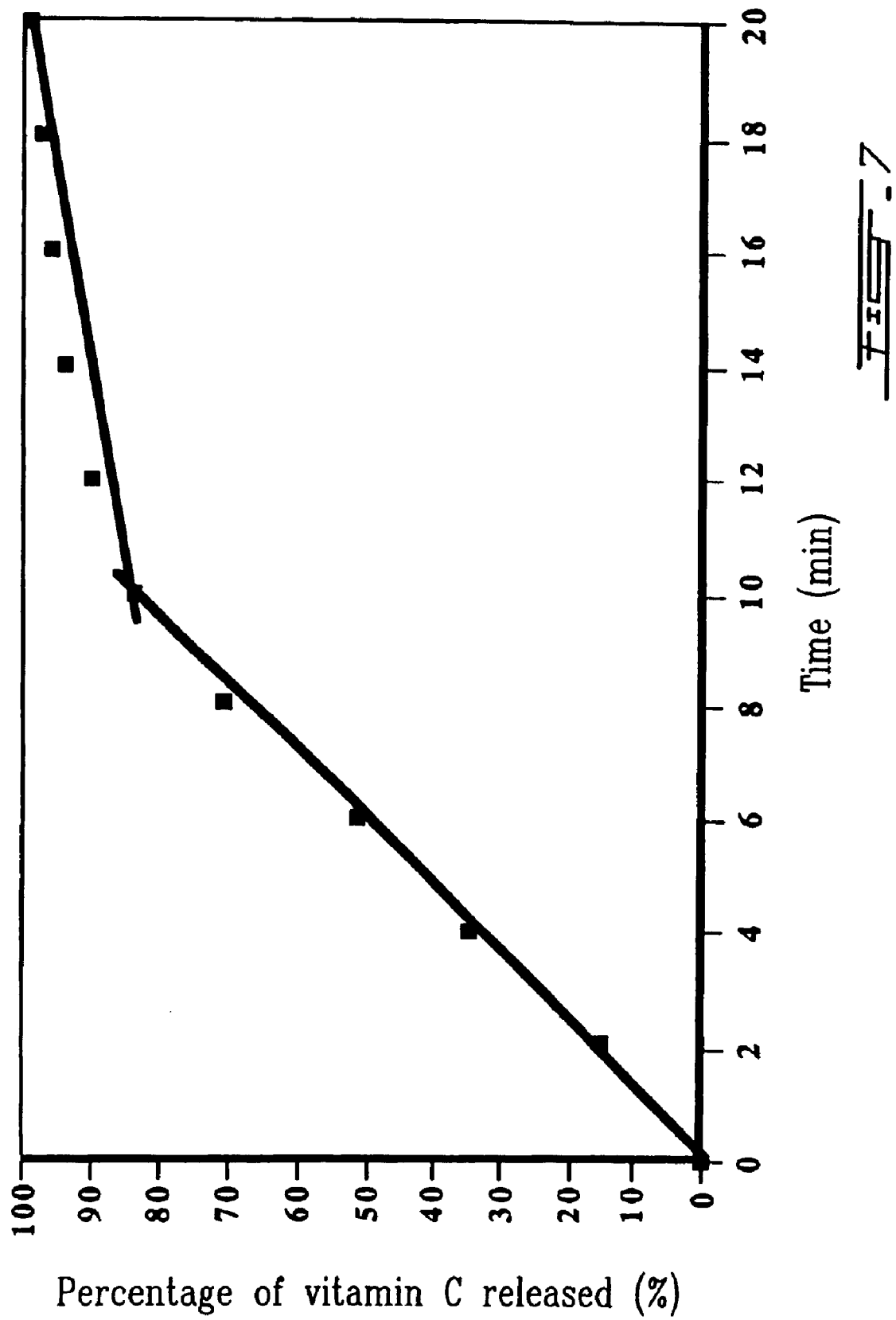
FIG. 7 is the variation of the % of Vitamin C released as a function of time. Sample coded VS2M. The hydrogel CHITOXAN™ —Vitamin C is prepared with CHITOXAN™ having a swelling index ($\alpha$) of 3500%.

FIG. 7 shows the liberation of Vitamin C for preparation VS2M. The release of 85% of the Vitamin C is achieved in the first 10 min.

The differences between the liberation profiles of the preparations are related to the swelling index. Sample VS2M, with a swelling index of 3500%, displayed a faster diffusion rate of Vitamin C than sample VS2R, α=2200%, and the latter more rapid in turn than that of sample VS2L, α=1800%. Thus the swelling index plays a key structural role in the release kinetics.

(g) Inclusion of CHITOXAN™ —Vit. C in a food mixture

Hydrogel CHITOXAN™ —Vit. C as well as other chitosan-xanthan hydrogels containing vitamins, nucleic acids, amino-acids and polypeptides can be used in hydrated food mixtures such as gels, sauces, syrups, etc. as well as in dehydrated mixtures.

The physical characteristics of the chitosan-xanthan hydrogel will determine the structure and more or less viscous texture of the final products. The choice of a hydrogel as described in the present invention will permit to adapt the hydrogel to diversified food applications.

Furthermore, the present invention also covers the production of tablets using CHITOXAN™ —Vit. C powder and other active ingredients as well when required. Thus, tablets made of freeze-dried powder of other chitosan- xanthan hydrogels containing different vitamins, amino-acids, nucleic acids and polypeptides and their combinations can be prepared.

Although the present invention has been described hereinabove by way of preferred embodiments thereof, it can be modified, without departing from the spirit and nature of the subject invention as defined in the appended claims. It is obvious that the present application can accommodate numerous other variations within the framework of the invention as described.

What is claimed is:

1. A dermatological cream comprising a controlled release composition comprising up to 25 wt % of a thermal or photosensitive active ingredient selected from vitamins, amino acids, nucleic acids, peptides and mixtures thereof, and comprising a chitosan-xanthan hydrogel, and comprising a stabilizing agent having a protective thermal and photo effect on said thermal or photosensitive ingredient, said hydrogel comprising 24–40% wt chitosan and 60–76% wt xanthan.

2. The dermatological cream of claim 1 wherein said thermo and photosensitive substance is vitamin A.

3. A dermatological cream in accordance with claim 1 wherein said thermo and photosensitive substance is an amino-acid.

4. A dermatological cream in accordance with claim 1 wherein the stabilizing agent is an acid.

5. A dermatological cream in accordance with claim 4 wherein the stabilizing acid is selected from the group of acids consisting of tartaric acid, metaphosphoric acid, citric acid and mixtures thereof.

6. A dermatological cream in accordance with claim 1 wherein the stabilizing agent is a peptide.

7. A dermatological cream in accordance with claim 6 wherein the stabilizing agent is a tripeptide.

8. A dermatological cream in accordance with claim 1 wherein the thermal or photosensitive active ingredient is liposoluble.

9. A dermatological cream in accordance with claim 1 wherein the thermal or photosensitive active ingredient is hydrosoluble.

* * * * *